United States Patent [19]
Lyon et al.

[11] Patent Number: 5,981,290
[45] Date of Patent: Nov. 9, 1999

[54] MICROSCALE COMBUSTION CALORIMETER

[75] Inventors: Richard E. Lyon; Richard N. Walters, both of Absecon, N.J.

[73] Assignee: The United States of America as represented by the Secretary of Transportation, Washington, D.C.

[21] Appl. No.: 08/827,885

[22] Filed: Apr. 7, 1997

[51] Int. Cl.[6] .......................... G01K 17/00; G01N 25/22
[52] U.S. Cl. ...................... 436/157; 374/45; 374/31; 374/14; 422/51
[58] Field of Search .................. 374/45, 31, 14, 374/34; 422/51; 436/155, 157, 160

[56] References Cited

U.S. PATENT DOCUMENTS

| | | | |
|---|---|---|---|
| 2,458,610 | 7/1949 | Lindstrom | 436/160 |
| 3,096,157 | 7/1963 | Brown et al. | 436/160 |
| 3,853,474 | 12/1974 | Austin | 436/160 |
| 3,933,429 | 1/1976 | Shibata et al. | 436/160 |
| 4,229,967 | 10/1980 | Kneifel et al. | 73/15 R |
| 4,499,191 | 2/1985 | Bruning et al. | 436/160 |
| 4,761,078 | 8/1988 | Farris et al. | 374/33 |
| 5,235,862 | 8/1993 | Harada | 436/157 |

FOREIGN PATENT DOCUMENTS

| | | | |
|---|---|---|---|
| 60-173466 | 9/1985 | Japan | 436/160 |
| 62-50660 | 3/1987 | Japan | 436/157 |
| 3009861 | 1/1988 | Japan | 436/157 |
| 63-37246 | 2/1988 | Japan | 436/157 |
| 0476220 | 7/1975 | U.S.S.R. | 436/157 |
| 1350577 A1 | 11/1987 | U.S.S.R. | 436/157 |

OTHER PUBLICATIONS

Bohdan Balko et al., Journal of Biochemical and Biophysical Methods vol. 4, No. 1, pp. 1–28, 1981.

*Primary Examiner*—Diego Gutierrez
*Assistant Examiner*—Maria Fernandez
*Attorney, Agent, or Firm*—Otto M. Wildensteiner

[57] ABSTRACT

A calorimeter for measuring flammability parameters of materials using only milligram sample quantities. The thermochemical and thermophysical processes associated with the flaming combustion of solids are reproduced in the device through rapid anaerobic pyrolysis in a thermogravimetric analyzer. Volatile anaerobic thermal decomposition products are swept from the pyrolysis chamber by an inert gas and combined with excess oxygen in a combustion chamber maintained at several hundred degrees Centigrade to simulate the combustion reactions which occur in a well ventilated diffusion flame. Mass loss is measured continuously during the process and heat release rate is calculated from the oxygen consumed from the gas stream.

13 Claims, 5 Drawing Sheets

| Number | Polymer Sample | Peak HRR (W/g) | Total HR (kJ/g) | Char Yield (%) | Comb Eff (-) | Total HOC (kJ/g) | Average HRR (kW/m²) |
|---|---|---|---|---|---|---|---|
| 1 | Polytetrafluoroethylene (PTFE) | 37 | 4.9 | 0.0 | 0.988 | 5.0 | 75.7 |
| 2 | Polyethersulfone (PES) | 62 | 4.5 | 41.9 | 0.167 | 27.0 | 20.0 |
| 3 | PX-1200 | 86 | 4.6 | 79.1 | 0.121 | 38.3 | 90.7 |
| 4 | Polyetherketoneketone (PEKK) | 87 | 5.8 | 64.8 | 0.186 | 31.2 | 33.0 |
| 5 | Polyetheretherketone (PEEK) | 144 | 9.5 | 56.2 | 0.304 | 31.1 | 160.0 |
| 6 | PX-1000 | 152 | 7.0 | 74.7 | 0.183 | 38.3 | 150.2 |
| 7 | Polyetherimide (PEI) | 187 | 10.1 | 59.2 | 0.341 | 29.6 | 79.5 |
| 8 | Phenolic Triazine (PT-30) | 278 | 5.9 | 62.5 | 0.191 | 30.7 | 200.0 |
| 9 | Polyacetal (POM) | 450 | 17.1 | 0.2 | 0.981 | 17.4 | 350.0 |
| 10 | Polysulfone (PSUL) | 499 | 19.2 | 34.7 | 0.864 | 22.3 | 240.0 |
| 11 | Polybutyleneterephthalate (PBT) | 607 | 33.7 | 3.4 | 1.207 | 27.9 | 713.0 |
| 12 | Polyphenyleneoxide (PPO) | 636 | 16.4 | 30.9 | 0.475 | 34.6 | 300.0 |
| 13 | Polyethyleneterephthalate (PET) | 804 | 14.5 | 12.2 | 0.658 | 22.0 | 242.0 |
| 14 | Polymethylmethacrylate (PMMA) | 1092 | 26.0 | 1.7 | 1.043 | 24.9 | 665.0 |
| 15 | Polyhexamethyleneadipamide (Nylon) | 1277 | 22.1 | 0.0 | 0.746 | 29.6 | 613.8 |
| 16 | Acrylonitrilebutadienestyrene (ABS) | 1660 | 37.6 | 0.6 | 0.946 | 39.8 | 848.8 |
| 17 | Polystyrene (PS) | 2201 | 41.3 | 0.5 | 1.037 | 39.9 | 800.0 |
| 18 | Polypropylene (PP) | 2567 | 48.0 | 0.0 | 1.108 | 43.3 | 1304.0 |
| 19 | Polyethylene (PE) | 2602 | 40.4 | 0.2 | 0.933 | 43.3 | 1133.0 |

MICROSCALE COMBUSTION CALORIMETER

STATEMENT OF GOVERNMENT INTEREST

The present invention may be made or used by or on behalf of the Government of the United States without the payment of any royalties thereon or therefor.

BACKGROUND

Heat release rate is the single most important parameter determining the fire hazard of a material. Several different bench scale methods of determining the heat release rate of burning specimens have been developed and are in use. All of these bench scale methods require samples on the order of 100 grams and thermal diffusion in these thick specimens dominates the thermal history of the material. Moreover, results from these bench scale tests depend not only on the sample mass and thickness but also on the spatial orientation of the specimen, boundary conditions, ignition source, and other parameters of the test setup totally unrelated to the properties of the material. Consequently, the flammability parameters determined in these devices are operationally-defined extrinsic quantities and not the intrinsic properties needed by materials scientists to develop fire resistant polymers.

A thermogravimetric analysis (TGA) technique for determining flammability characteristics of milligram samples of polymeric materials has been reported which uses the TGA sample furnace as the combustion reactor. Carbon dioxide ($CO_2$) and carbon monoxide (CO) generation are measured and used to calculate heat release during aerobic pyrolysis of 50 mg polymer composite samples during slow transient heating in the TGA furnace. Although this thermogravimetric technique probably represents the first published attempt to directly measure heat release rate during combustion of milligram samples, the method suffers from several problems as a flammability test: 1) Aerobic pyrolysis conditions and the high surface to volume ratio of the specimen used in the published TGA method result in rapid and complete volatilization of oxidizable organic material to gaseous products leaving no residual char. Total thermo-oxidative degradation as occurs in the published TGA method does not represent the thermochemical fuel generation process in burning materials. Burning materials are characterized by a pyrolysis zone in which anaerobic reducing conditions exist to produce a residual carbonaceous mass (char) in aromatic or cyclic polymers. As char production is an important and well known mechanism for reducing the flammability of polymers, it is important to reproduce the necessary conditions leading to char formation in order to have a meaningful flammability test. 2) The TGA flammability technique utilizes a heating rate of only 20 K/min and this is well below the 600 K/min pyrolysis zone heating rate estimated for polymer burning. Thermogravimetric studies have shown that the mass loss history or fuel generation rate of char-forming polymers is significantly different at heating rates of 600 K/min than at 20 K/min and cannot be predicted from mass loss kinetics obtained at the lower heating rate. Consequently the rates of polymer fuel generation and heat release measured in the published TGA flammability technique at low heating rates would be significantly different from those which occur in a fire involving the same material. 3) Only time-averaged values for the heat release rate calculated from $CO_2$ and CO production in the relatively slow non-flaming aerobic TGA thermo-oxidative decomposition experiment are used to calculate heat release rate in the thermogravimetric technique. The relationship between this average heat release rate per unit area of sample pan in the TGA method and bench-, intermediate-, or full-scale heat release rate tests of materials and components is obscure. 4) Since oxidative combustion reactions occur in the TGA furnace at the pyrolysis temperature there is no flame temperature oxidative combustion step in the published TGA method as occurs in the combustion zone of burning polymers where volatile anaerobic decomposition products from the pyrolysis zone mix with oxygen to produce a diffusion flame. 5) Carbon dioxide/carbon monoxide generation calorimetry, although more sensitive than oxygen consumption calorimetry, is inherently less accurate and requires more equipment and detailed knowledge about the chemical composition of the sample material. 6) The heat flux at the sample surface in the published thermogravimetric method is poorly defined compared to bench-scale fire tests where constant, calibrated, heat fluxes are employed.

OBJECTS OF THE INVENTION

Accordingly, it is an object of the present invention to provide a means and method for more accurately simulating the actual conditions which occur during the combustion of a material.

It is a further object of the present invention to provide a means and method to more accurately simulate the char formation which occurs at the surface of a burning material.

It is a further object of the present invention to provide a means and method to more accurately simulate the high heating rate at the surface of burning materials.

It is a further object of the present invention to provide a means and method to more accurately simulate the high temperature combustion that occurs in the diffusion flame above a burning material.

SUMMARY

Briefly, the present invention is a calorimeter that uses very small, on the order of 10 milligram, samples to determine the combustion characteristics of materials, primarily polymers. The sample is first pyrolyzed in a calibrated constant heat flux in a non-oxidizing atmosphere which simulates sub-surface conditions in the pyrolysis zone of a burning material. The resulting volatile anaerobic thermal decomposition products are swept from the pyrolysis chamber by an inert gas to a manifold maintained at greater than 250 degrees Centigrade where they are mixed with excess oxygen. This mixture is then swept into a combustion furnace maintained at 700–1200° C. to complete the combustion reactions which occur in a well ventilated diffusion flame. A lower temperature can be used if a catalyst (e.g. platinum) is used in the combustion furnace. Measuring the amount of oxygen that is added and measuring the amount of oxygen remaining after combustion allows the calculation of heat release rate, effective heat of combustion, etc. Separately controlling the thermochemical reactions and thermophysical phenomena involved in the burning of organic materials in this way allows decoupling of the intrinsic chemical processes of material combustion from the transient effects associated with thermal diffusion in large samples. This in turn will perhaps allow each to be studied separately.

IN THE DRAWINGS

FIG. 5 shows heat release rate measurements on a series of polymers.

DESCRIPTION OF THE PREFERRED EMBODIMENT

Figure 1:
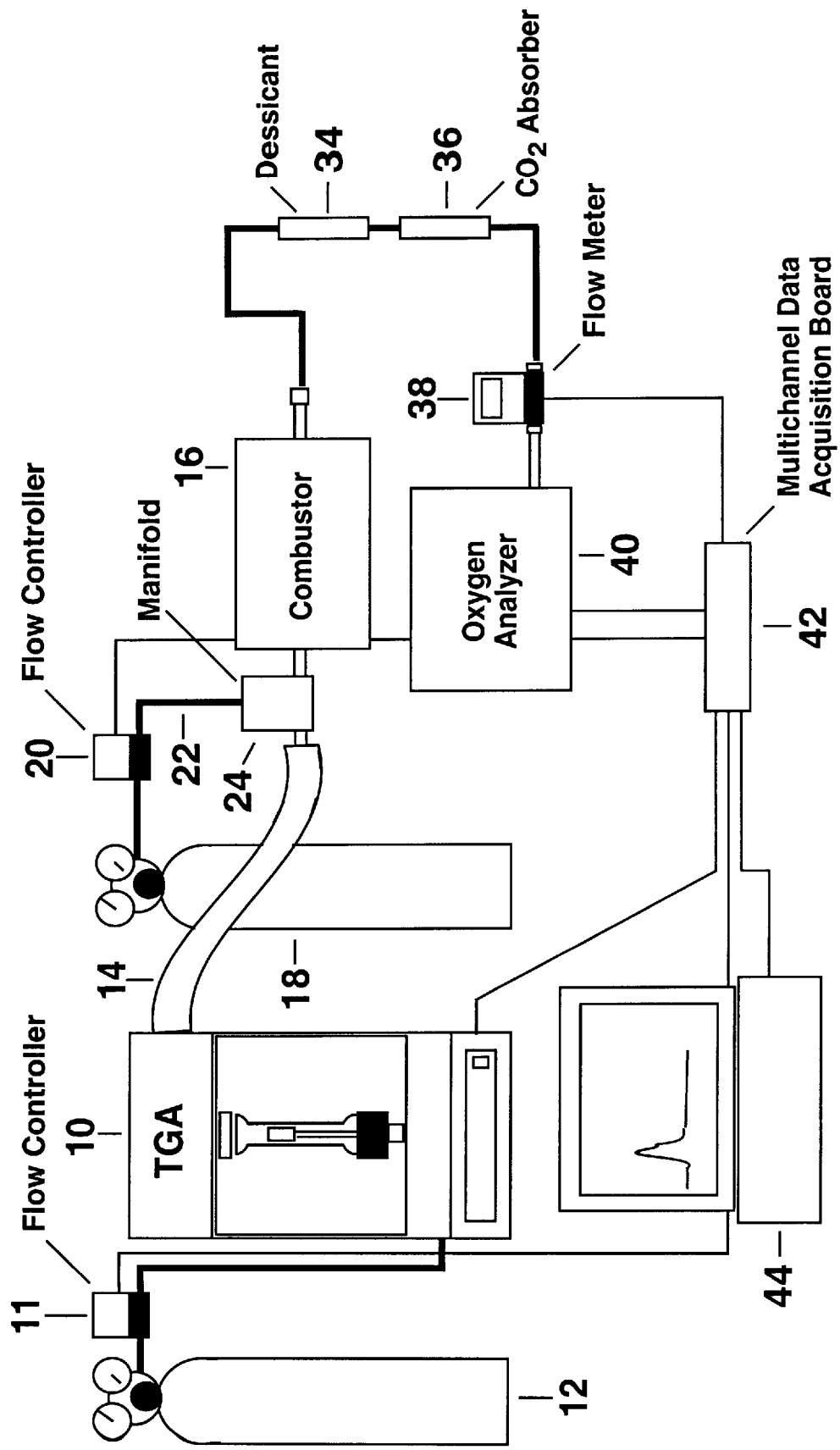
FIG. 1 shows the overall layout of the microscale combustion calorimeter of the present invention.

FIG. 1 shows the microscale combustion calorimeter of the present invention. It comprises a thermogravimetric analyzer (TGA) 10 (Perkin-Elmer TGA System 7 or similar device with rapid heating capability) wherein the sample is thermally decomposed. The products of decomposition are swept through TGA 10 by an inert purge gas, typically 99.99% pure nitrogen, from cylinder 12 and flow controller 11 through heated transfer line 14 to combustor 16. Prior to entering combustor 16 an excess of oxygen is added to the products of decomposition from cylinder 18 through flow controller and temperature sensor 20 via line 22. The oxygen is mixed with the decomposition products in manifold 24, which is maintained at greater than 250° C., and then flows into combustor 16.

Figure 2:
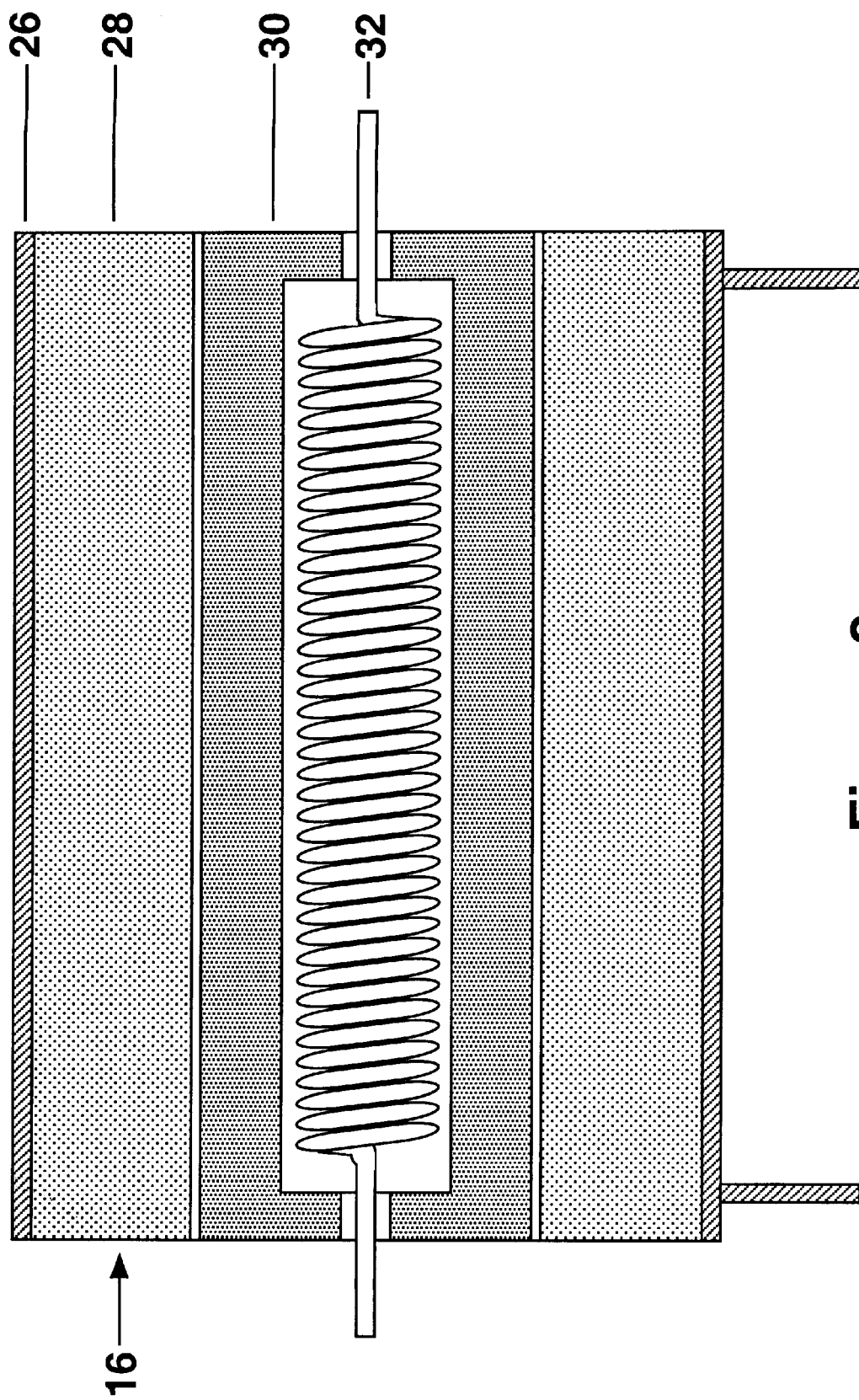
FIG. 2 shows the tubular coil combustor.

FIG. 2 shows a cross section of combustor 16. It comprises an aluminum shell 26 surrounding a 5 cm layer of ceramic fiber insulation 28 in the middle of which is ceramic heater 30 which surrounds a coil of Inconel tubing 32. Heater 30 is capable of maintaining a maximum temperature of 1200° C. Tubing 32 is 5 meters long (24 cm long and 5 cm in diameter when coiled) and 6.35 mm OD with a wall thickness of 0.89 mm, which gives a residence time in heater 30 of approximately 60 seconds at a total flow rate of 100 cc per minute. Published data indicate that this time is required to completely burn the largest soot particles observed in real fires.

After exiting combustor 16 the gases are optionally cooled to remove condensable combustion products ($H_2O$, halogen acids, etc.), then passed through a dessicant (e.g. Drierite™) 34 to remove water and then through a $CO_2$ absorber (e.g. Ascerite™) 36 to remove $CO_2$. At this point the only gases in the stream are the inert purge gas (usually nitrogen) and the excess oxygen not consumed in the combustion furnace during the reaction.

The gas stream then passes through flow meter and temperature sensor 38 and then into oxygen analyzer 40 (Rosemount Analytical OM-11 EA or equivalent).

Data from TGA 10, flow controllers 11 and 20, flow meter 38, and oxygen analyzer 40 are continuously gathered by multichannel data acquisition board 42 and sent to computer 44 for analysis.

Oxygen consumption calorimetry, used in the present invention, is based on the well-known experimental observation that the heat of complete combustion of typical organic molecules per mole of oxygen consumed is essentially independent of the starting chemical composition of the material. In the present invention the heat release rate due to combustion of the polymer decomposition products is calculated by measuring the difference in the mass flow rate of oxygen before and after the combustion reaction with the pyrolyzate at high temperature and multiplying by 13.1±0.6 KJ/g-$O_2$ (Thornton's rule), a value which is valid for a large range of polymers and organic materials.

Heat release rate measurements using the present invention were conducted on a series of polymers (see FIG. 5). Specimen sizes of 2–20 mg were heated at 200° C. per minute under nitrogen gas purge at 80 cc per minute to a set point temperature of 600° C. Mass loss was measured continuously during the rapid heating and pyrolysis. The combustor was maintained at 900° C. and gas temperatures, flow rates, and oxygen concentrations before and after the combustor were continuously monitored.

Figure 3:
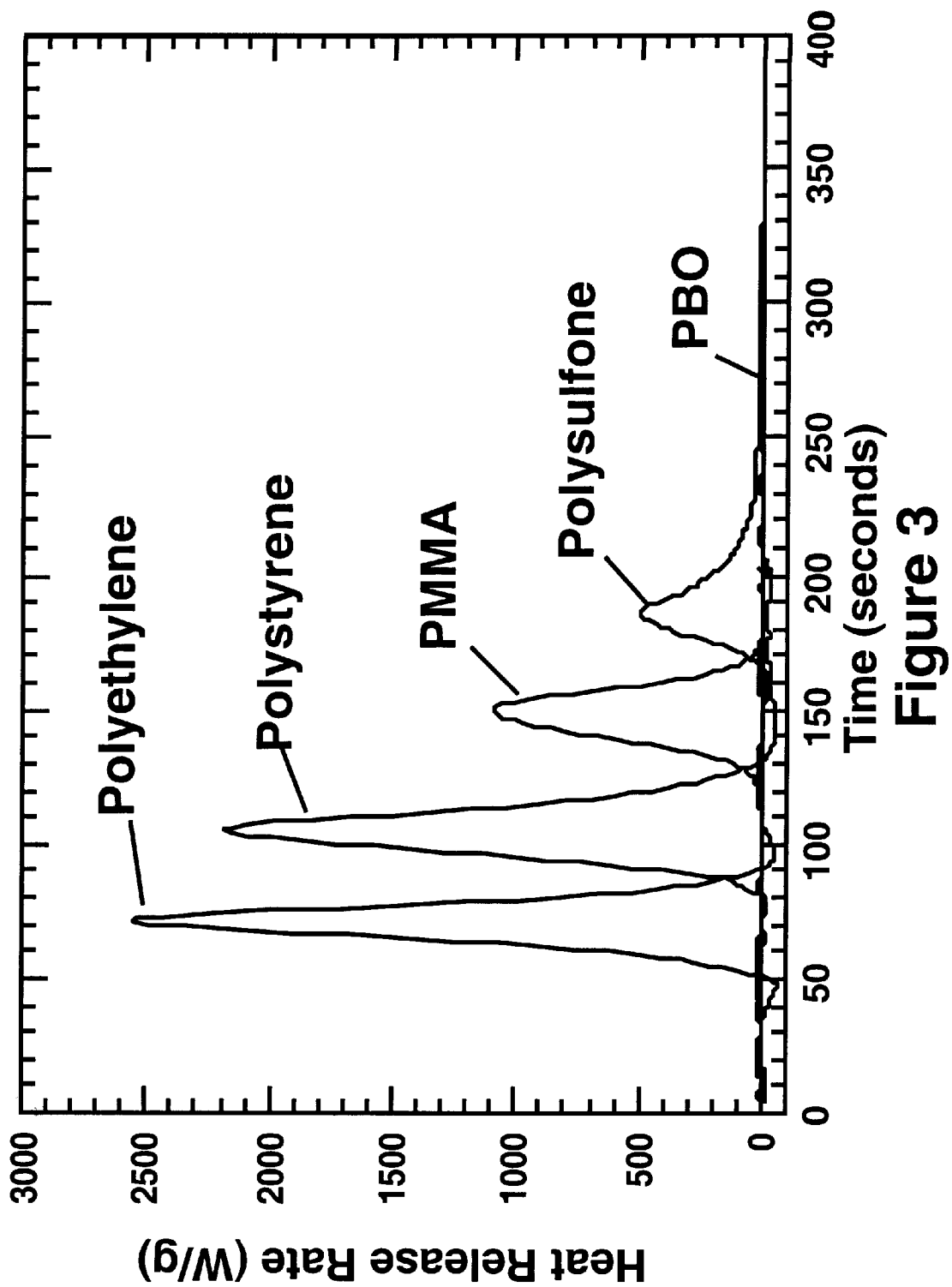
FIG. 3 shows representative heat release rates measured with the microscale combustion calorimeter of the present invention.
Figure 4:
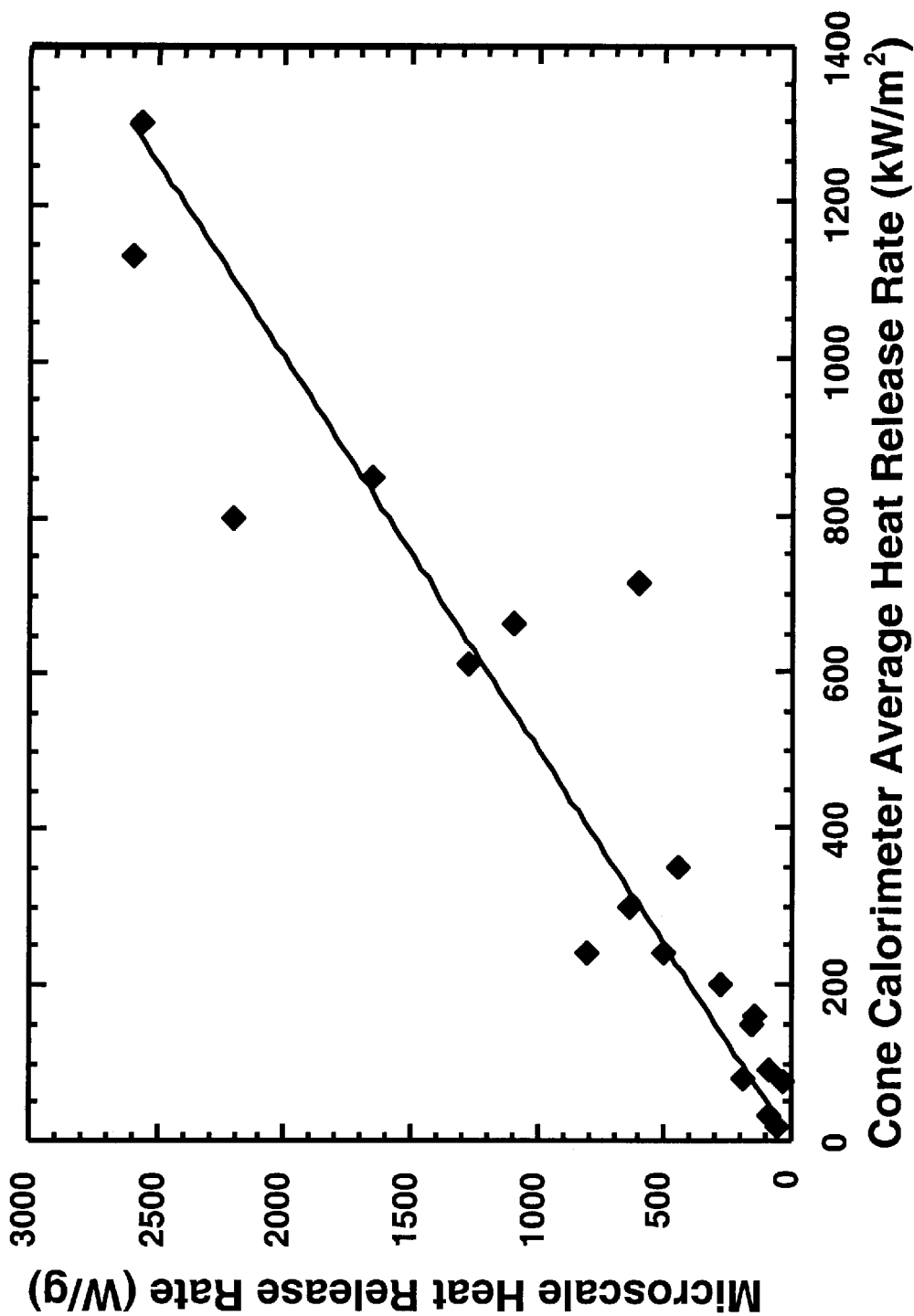
FIG. 4 shows the correlation between polymer average heat release rate in the cone calorimeter and peak heat release rate in the microscale calorimeter of the present invention at a 50 KW/m² incident heat flux.

FIG. 3 shows heat release rate data for various materials obtained from the microscale calorimeter of the present invention. FIG. 4 compares the peak rate of heat helease (RHR) from the microscale calorimeter of the present invention with the average heat release data from large (decagram) samples measured in a conventional cone calorimeter at comparable conditions. The cone calorimeter heat release rate values reported are average values obtained by dividing the effective heat of combustion by the time of burning. There appears to be a good correlation between the peak heat release rates measured in the microscale combustion calorimeter of the present invention and the average values measured in the bench scale cone calorimeter. As cone calorimeter heat release rate data correlate well with full scale fire tests, microcalorimetric heat release rates as determined by the microscale calorimeter of the present invention should also be a good predictor of full scale fire performance.

TABLE

| Number | Polymer Sample | Peak Heat Release (W/g) | Char Yield (%) | Total Heat of Complete Combustion (kJ/g) |
|---|---|---|---|---|
| 1 | PX-1200 | 86.3 | 78.1 | 38.3 |
| 2 | Polyetherketoneketone (PEKK) | 86.9 | 62.3 | 31.2 |
| 3 | Polyetheretherketone (PEEK) | 143.8 | 52.9 | 31.1 |
| 4 | PX-1000 | 152.9 | 72.3 | 38.3 |
| 5 | Polyethersulfone (PES) | 195.2 | 39.8 | 25.4 |
| 6 | Phenolic Triazine (PT-30) | 277.7 | 62.4 | 30.7 |
| 7 | Polyetherimide (PEI) | 437.9 | 55.6 | 29.6 |
| 8 | Polyethyleneterephthalate (PET) | 689.1 | 9.3 | 24.1 |
| 9 | Polybutyleneterephthtalate (PBT) | 947.5 | 3.4 | 27.9 |
| 10 | Polymethylmethacrylate (PMMA) | 1436.2 | 0.3 | 26.7 |
| 11 | Polystyrene (PS) | 2147.6 | 0.8 | 43.7 |
| 12 | Polypropylene (PP) | 2896.9 | 0.3 | 45.8 |
| 13 | Polyethylene (PE) | 3031.4 | 0.2 | 42.2 |

We claim:

1. A calorimeter for analyzing samples in the milligram range comprising means for thermally decomposing said sample under controlled conditions, a furnace, means for transporting the products of decomposition of said sample to said furnace, means for mixing oxygen with said products of decomposition prior to combustion in said furnace, means for collecting the gaseous effluent from said furnace, means for removing $H_2O$ and $CO_2$ from said effluent, and means for measuring the composition of said effluent after removal of said $H_2O$ and $CO_2$.

2. A calorimeter as in claim 1 further including means for preventing condensation of the volatile components of said products of decomposition while being transported to said furnace.

3. A calorimeter as in claim 2 wherein said means for transporting said products of decomposition of said sample comprises a gas stream.

4. A calorimeter as in claim 3 further including means for measuring the mass flow rate and temperature of the oxygen being mixed with said products of decomposition.

5. A calorimeter as in claim 4 wherein said furnace is sized to have a residence time of said effluent in said furnace sufficient to completely oxidize all of the particulates in said effluent.

6. A calorimeter as in claim 5 wherein said residence time is about 60 seconds.

7. A calorimeter as in claim 5 further including means for cooling said effluent from said furnace before measuring the composition of said effluent.

8. A method of measuring the flammability parameters of milligram samples of materials which comprises thermally decomposing said sample under controlled conditions, mixing the products of decomposition of said sample with oxygen, transporting said products of decomposition to a furnace, burning said products in said furnace, and analyzing the effluent from said furnace to measure the flammability parameters of said sample.

9. The method of claim 8 wherein said controlled conditions comprise anaerobic conditions.

10. The method of claim 9 further including preventing the condensation of the volatile components of said products of decomposition prior to being burned in said furnace.

11. The method of claim 10 further including maintaining said products of decomposition in said furnace for a time sufficient to completely oxidize all of the particulates in said products of decomposition.

12. The method of claim 11 further including removing the $H_2O$ and $CO_2$ from said effluent from said furnace prior to said analysis.

13. The method of claim 12 further including measuring the mass flow rate and temperature of the oxygen that is added to said products of decomposition.

* * * * *